(12) United States Patent
Pessin

(10) Patent No.: US 9,566,424 B2
(45) Date of Patent: Feb. 14, 2017

(54) HEMOSTASIS VALVE DEVICE FOR INJECTING A MEDICAL MATERIAL INTO A PATIENT, AND RELATED METHOD

(75) Inventor: Olivier Pessin, Grezieu la Varenne (FR)

(73) Assignee: Perouse Medical, Ivry le Temple (FR)

( * ) Notice: Subject to any disclaimer, the term of this patent is extended or adjusted under 35 U.S.C. 154(b) by 241 days.

(21) Appl. No.: 14/127,564

(22) PCT Filed: Jun. 22, 2012

(86) PCT No.: PCT/EP2012/062127
§ 371 (c)(1),
(2), (4) Date: Feb. 25, 2014

(87) PCT Pub. No.: WO2012/175699
PCT Pub. Date: Dec. 27, 2012

(65) Prior Publication Data
US 2014/0207083 A1  Jul. 24, 2014

(30) Foreign Application Priority Data
Jun. 22, 2011  (FR) ...................... 11 55495

(51) Int. Cl.
*A61M 39/06*  (2006.01)
(52) U.S. Cl.
CPC ......... *A61M 39/06* (2013.01); *A61M 39/0606* (2013.01); *A61M 39/0613* (2013.01)
(58) Field of Classification Search
CPC .............. A61M 39/06; A61M 39/0606; A61M 39/0613; A61M 2039/062; A61M 2039/0626
See application file for complete search history.

(56) References Cited

U.S. PATENT DOCUMENTS 3,920,215 A * 11/1975 Knauf ................. A61M 39/285
                                                         251/251
4,723,550 A *  2/1988 Bales ................. A61M 39/0613
                                                         604/256
(Continued)

FOREIGN PATENT DOCUMENTS

CN        201572436 U     9/2010
JP      2000/316986 A    11/2000
(Continued)

OTHER PUBLICATIONS

International Search Report and Opinion in related application PCT/EP2012/062127.
(Continued)

*Primary Examiner* — Andrew Gilbert
(74) *Attorney, Agent, or Firm* — Eric L. Lane; Green Patent Law

(57) ABSTRACT

The device according to the invention includes a hollow body delimiting an inner passage. It further includes an assembly for maintaining the material in position in the inner passage.
The maintaining assembly includes a radially compressible member delimiting, when idle, a through passage aperture of the material, and a radial compression member compressing the compressible member, radially movable relative to an axis of the passage aperture to outwardly compress the compressible member.
It includes a member for actuating the or each compression member, radially movable relative to the body to cause the compression member to go from a radially retracted position, in which the section of the passage aperture is maximal, to a position radially deployed in the compressible member, in which the section of the passage aperture is minimal.

17 Claims, 7 Drawing Sheets

(56) References Cited

U.S. PATENT DOCUMENTS

| | | | | |
|---|---|---|---|---|
| 5,125,915 A | * | 6/1992 | Berry | A61M 39/0613 285/309 |
| 5,127,626 A | * | 7/1992 | Hilal | A61B 17/3462 251/149.1 |
| 5,201,714 A | * | 4/1993 | Gentelia | A61B 17/3462 251/149.2 |
| 5,324,271 A | | 6/1994 | Abiuso et al. | |
| 5,921,968 A | * | 7/1999 | Lampropoulos | A61M 39/0613 604/167.05 |
| 6,834,842 B2 | * | 12/2004 | Houde | A61M 39/0613 251/149.1 |
| 6,860,463 B2 | * | 3/2005 | Hartley | F16K 7/06 251/294 |
| 8,807,517 B2 | * | 8/2014 | Townsend | F16K 7/065 251/251 |
| 2001/0021825 A1 | * | 9/2001 | Becker | A61M 39/06 604/167.01 |
| 2003/0116731 A1 | * | 6/2003 | Hartley | A61M 39/0613 251/7 |
| 2005/0085789 A1 | * | 4/2005 | Khan | A61M 39/0613 604/500 |
| 2009/0259200 A1 | | 10/2009 | Lampropoulos et al. | |

FOREIGN PATENT DOCUMENTS

| | | |
|---|---|---|
| JP | 2003/533328 A | 11/2003 |
| WO | WO 00/53254 A1 | 9/2000 |
| WO | WO 01/89397 A1 | 11/2001 |
| WO | WO 03/048616 A1 | 6/2003 |

OTHER PUBLICATIONS

Search Report mailed Apr. 4, 2016 in related Japanese Patent Application No. 2014-516373.

* cited by examiner

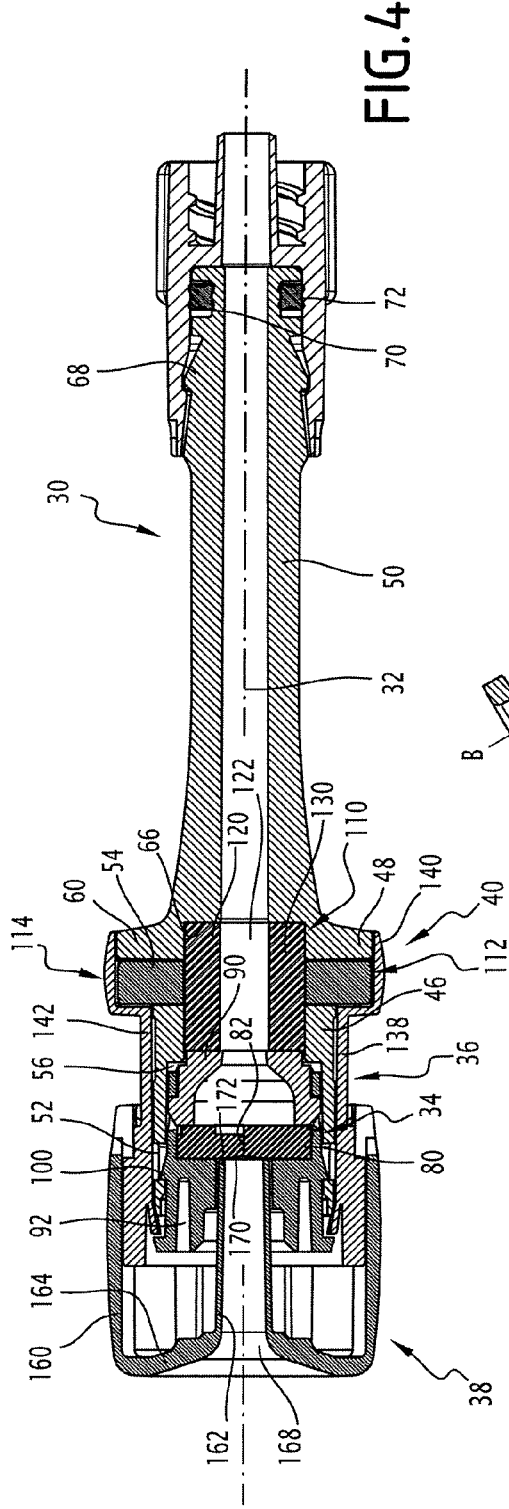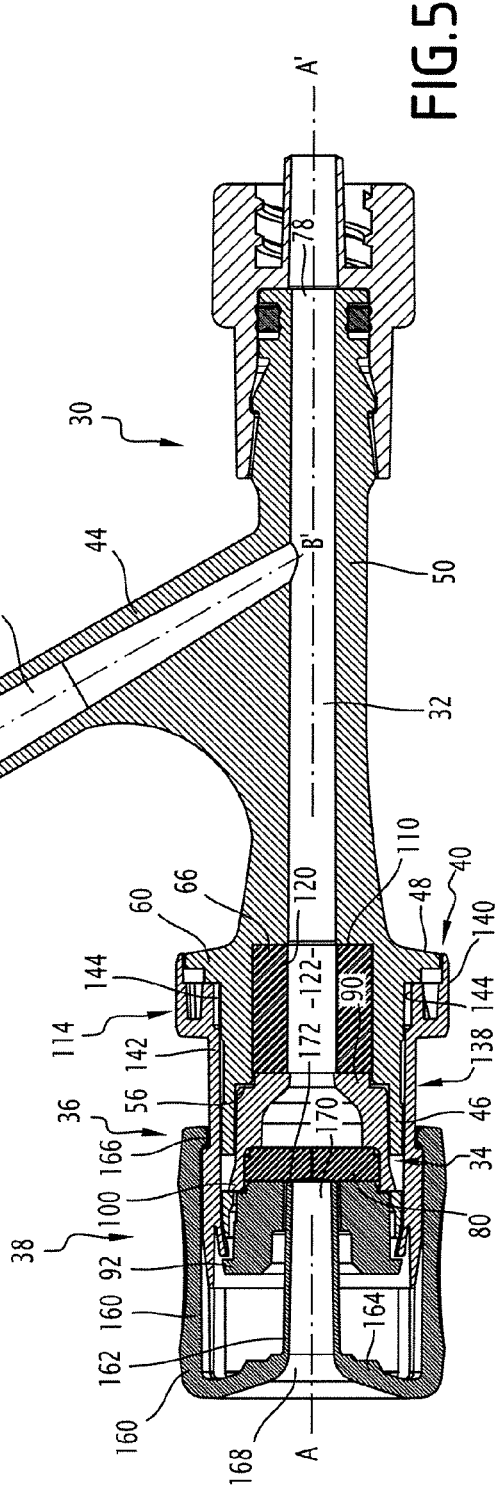

HEMOSTASIS VALVE DEVICE FOR INJECTING A MEDICAL MATERIAL INTO A PATIENT, AND RELATED METHOD

The present invention relates to a hemostasis valve device intended for inserting a medical material into a patient, comprising:
- a hollow body delimiting an inner passage for inserting the material extending between a proximal opening and a distal opening;
- a sealing valve, positioned in the inner passage, the sealing valve having at least one central passage that is sealed when idle;
- an opening member for the central passage of the valve, movable relative to the body between an idle position, in which the valve is sealed, and an open position of the valve.

Such a device is intended in particular to perform interventional cardiology and interventional radiology operations. It is in particular intended to provide blood sealing during the insertion of medical devices into the body of a patient.

The medical material is for example a catheter, a guide wire, a guide, a balloon catheter that is crimped or non-crimped of a stent, a rotary milling tool covered with diamond microcrystals, for example Rotablator®, or a combination of these devices.

This medical material is generally inserted into the body of the patient through the vascular system, in particular through a vein or artery, to convey them to the precise location of the operation in the patient's body.

To prevent leaks of bodily fluids, in particular blood, during the insertion of the material, it is necessary to place a hemostasis valve device of the aforementioned type at the insertion point of the material in the patient. U.S. Pat. No. 5,324,271 describes one example of a hemostasis valve device.

This device includes a proximal valve, intended to perform sealing around the material when it is inserted into the body. It further includes a distal valve, formed by a sleeve. The sleeve is axially compressible by an actuating member that can be screwed on the body.

The distal valve can be actuated once the material is inserted through the inner passage. To perform the sealing, the practitioner must screw the actuating member, which may be tedious to perform.

Furthermore, the axial compression of the valve makes it possible to achieve sealing around the device, but does not guarantee effective axial maintenance of the medical material in the device. Furthermore, the practitioner cannot easily determine whether the screwing that has been done is sufficient to ensure sealing around the material, or even to maintain the material itself.

One aim of the invention is therefore to obtain a hemostasis valve device that guarantees good sealing while preserving mobility of the material and, if needed, at a precise moment of the procedure, effective maintenance of the material it contains, while being easy and quick to use.

To that end, the invention relates to a device of the aforementioned type, characterized in that the device further includes an assembly for maintaining the material in position in the inner passage of the body, the maintaining assembly including:
- a radially compressible member positioned in the inner passage, the compressible member delimiting, when idle, a crossing passage aperture of the material;
- at least one radial compression member for radially compressing the compressible member, radially movable relative to an axis of the passage aperture to outwardly compress the compressible member;
- a member for actuating the or each compression member, radially movable relative to the body to cause the compression member to go from a radially retracted position, in which the section of the passage aperture is maximal, to a position radially deployed position in the compressible member, in which the section of the passage aperture is minimal.

The device according to the invention may comprise one or more of the following features, considered alone or according to any technically possible combination:
- the actuating member is movable in rotation around a longitudinal axis A-A' of the body,
- the actuating member is movable only in rotation around the longitudinal axis A-A' of the body, without translation relative to the body,
- it includes at least two opposite compression members, the actuating member being capable of simultaneously moving the compression members from their radially retracted position toward their radially deployed position,
- the compressible member includes an elastic sleeve which, when idle, delimits the passage aperture, the thickness of the sleeve, considered perpendicular to the axis of the passage aperture, being greater than 50% of the maximal transverse expanse of the passage aperture,
- the compressible member is formed from a material having a hardness comprised between 15 Shore A and 25 Shore A,
- the or each compression member includes a jaw having a concave surface intended to lean on a convex outer surface of the compressible member,
- the opening member of the valve is mounted movable in translation on the actuating member, the opening member being movable jointly with the actuating member during its movement between the first position and its second position,
- the valve includes a pierced body, in particular a pierced body made up of two pierced discs assembled one on the other, the pierced body delimiting a plurality of covering shutters, the opening member comprising a hollow actuating sleeve that inserts between the shutters to open the central passage of the valve,
- it includes means for locking the actuating member in position in its second position,
- the valve is positioned between the proximal opening of the body and the compressible member,
- the actuating member is mounted movable in rotation relative to the body around an axis D-D' perpendicular to the longitudinal axis A-A' of the body,
- the compressible member is positioned axially separated from the sealing valve along the hollow body.

The invention also relates to a method for axially maintaining a medical material, of the type comprising the following steps:
- providing a device as described above, the medical material being inserted through the inner insertion passage, the radially compressible member occupying an idle configuration in which the passage aperture occupies a maximal transverse section;
- moving the actuating member from its first position to its second position;

radially moving the or each radial compression member to radially deform the compressible member and press the compressible member against the medical material.

The invention also relates to a percutaneous treatment method comprising the following steps:
- providing a device as described above, and a medical material intended to be inserted into the body of the patient;
- advantageously, actuating the opening member of the passage to free the passage and inserting the material into the central passage of the valve;
- actuating the member to close the passage through the valve;
- extracting the medical material through the distal opening and inserting it in the body of the patient;
- actuating the actuating member from its first position toward its second position to move the or each compression member from its retracted position to its radially deployed position;
- compressing the compressible member to apply the compressible member around the material while reducing the section of the passage aperture.

The invention will be better understood upon reading the following description, provided solely as an example, and done in reference to the appended drawings, in which:

FIG. 4 is a cross-sectional view in a median horizontal plane of the device of FIG. 3;

FIG. 5 is a cross-sectional view along a median vertical plane of the device of FIG. 3;

Hereafter, the terms "proximal" and "distal" are to be understood as being relatively closer to the operator, and relatively further from the operator, respectively.

Figure 1:
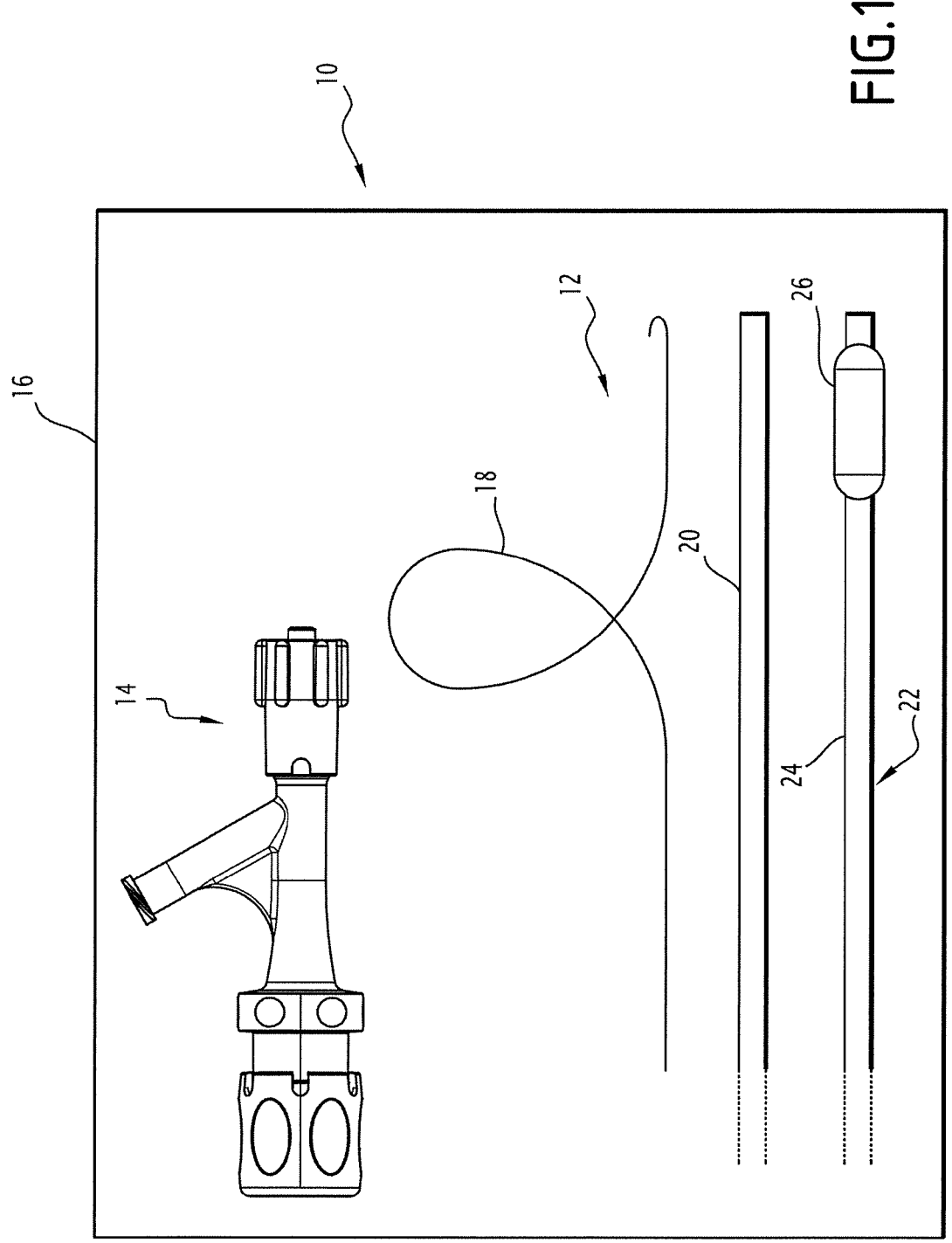
FIG. 1 is a diagrammatic top view of a first treatment kit according to the invention.

A first kit 10 according to the invention is shown in FIG. 1.

As illustrated by FIG. 1, the treatment kit 10 according to the invention includes at least one medical material 12 intended to be inserted into the body of a patient, and a hemostasis valve device 14 according the invention, to facilitate and monitor the inserted of the medical material 12 into the body of the patient.

The kit 10 according to the invention is advantageously contained in at least one sterile packaging 16 diagrammatically illustrated in FIG. 1.

The material 12 is intended to be inserted into the body of the patient, using a vein or artery.

The medical material 12 intended to be inserted into the patient is in particular used during operations on the vascular system of the patient, in particular in interventional cardiology and interventional radiology.

In particular, in the example illustrated in FIG. 1, the medical material comprises a guide catheter 20, a guide wire 18, a guide, a balloon catheter 22 that is crimped or non-crimped of a stent, a Rotoblator®.

Depending on the material 12 that is inserted, and the number of devices inserted at the same time, the radial expanse of the material 12 is quite variable.

As will be seen below, the hemostasis valve device 14 is adapted to accommodate material 12 having quite different radial expanses, for example, comprised between 0.25 mm and 2 mm.

Figure 2:
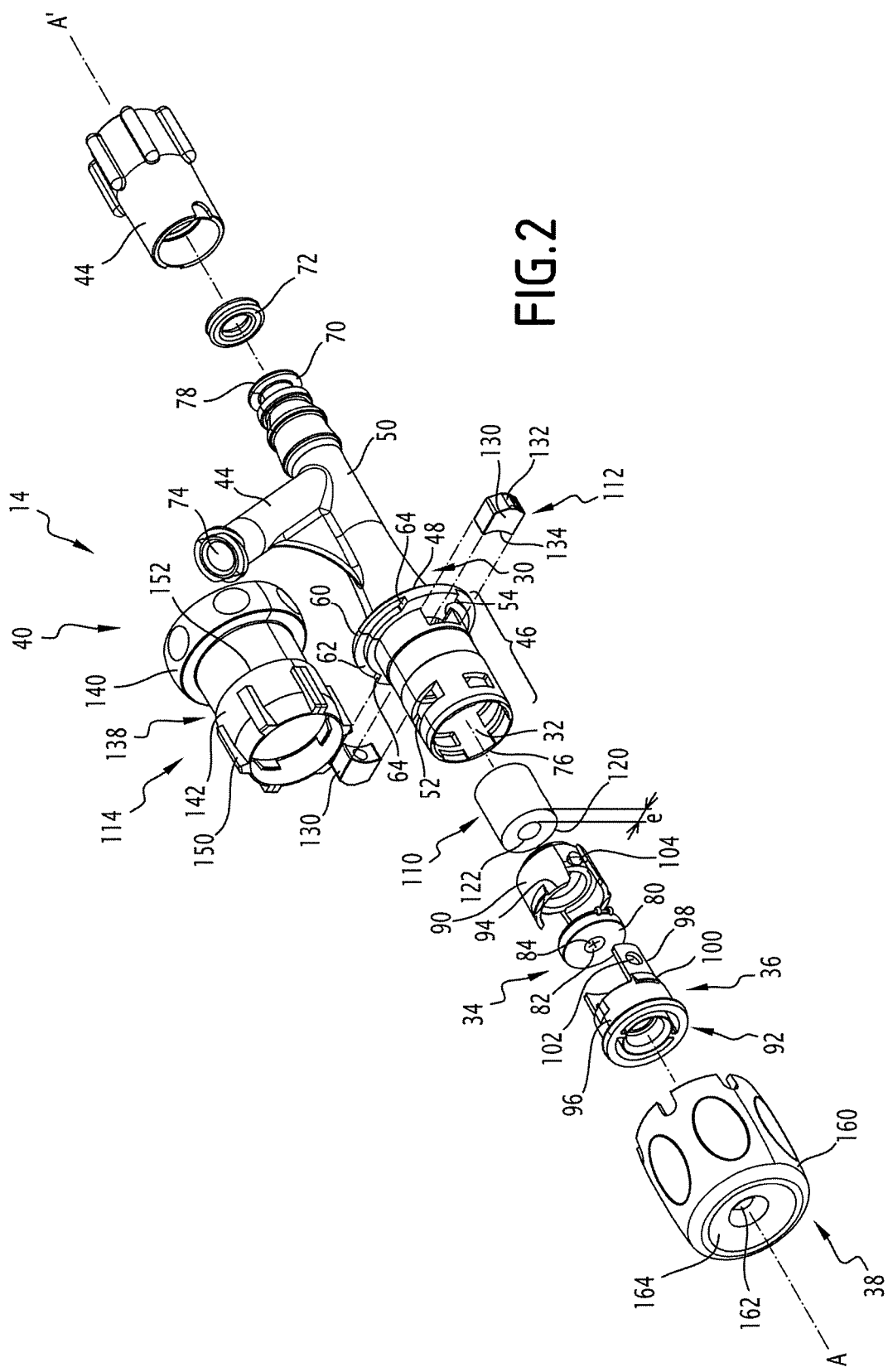
FIG. 2 is an exploded perspective view of the hemostasis valve device according to the invention present in the kit of FIG. 1.
Figure 3:
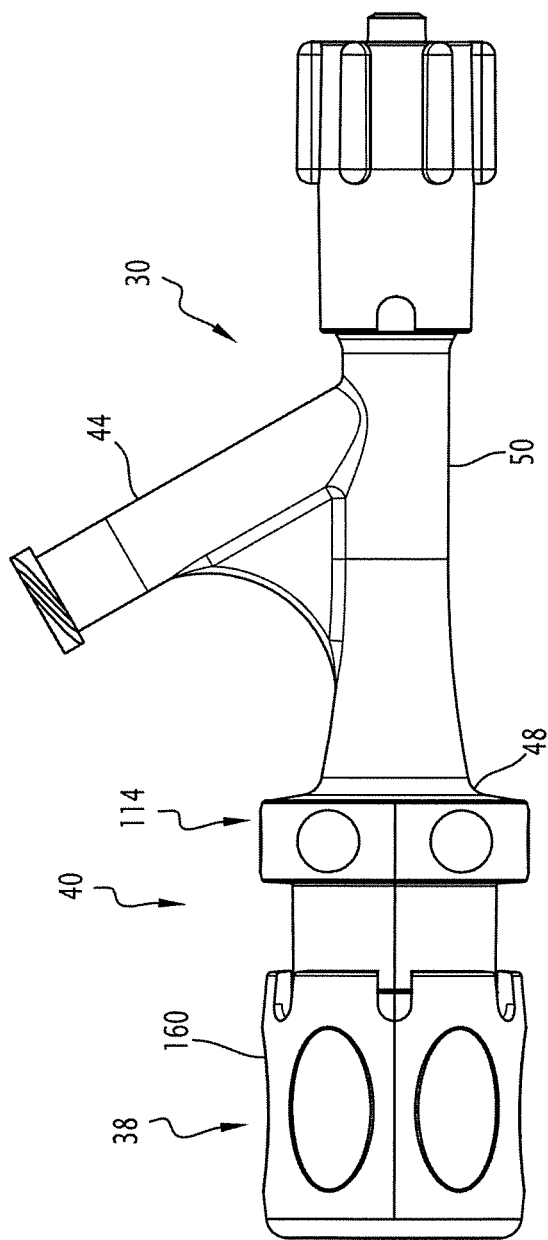
FIG. 3 is a side view of the device of FIG. 2.

As illustrated by FIGS. 2 and 3, the hemostasis valve device 14 according to the invention includes a generally tubular hollow body 30 delimiting an inner passage 32 for inserting material.

The device 14 further includes an elastic sealing valve 34, of the "push and pull" type, and a mechanism 36 for axial locking of the valve 34.

The device 14 also comprises a member 38 for opening the valve 34 and an assembly 40 for axially maintaining material 12 in the inner passage 32.

As illustrated by FIGS. 2 to 4, the body 30 includes a principal tubular element 42 and, advantageously, a transverse tapping 44 for inserting a liquid product into the inner passage 32. It is provided with a tip 44, in particular a tip mounted freely rotating at the distal end of the tubular element 42.

In reference to FIG. 2, the body 30 includes a proximal portion 46 that houses the elastic valve 34, an intermediate portion 48 to guide the axial maintaining assembly 40, and a distal portion 50 bearing the tip 44.

The proximal portion 46 is generally cylindrical. It delimits proximal openings 52 for retaining the locking mechanism 36 and distal windows 54 for the passage of the compression members of the axial maintaining assembly 40.

The proximal openings 52 and the distal windows 54 radially pass through the proximal portion 46 to emerge in the inner passage 32.

In the example shown in FIG. 2, the body 30 delimits two distal windows 54 positioned across from one another, on either side of the axis A-A' of the body.

In reference to FIG. 4, the proximal portion 46 advantageously delimits, in the inner passage 32, a proximal annular shoulder 56 for axially locking the elastic valve 34.

The intermediate portion 48 includes an annular collar 60 protruding radially outward, for guiding the axial maintaining assembly 40. The collar 60 has at least one guide track 62 angularly delimited by end-of-travel stops 64.

The intermediate portion 48 delimits, in the inner passage 32, a distal annular shoulder 66 for retaining the axial maintaining assembly 40. The distal windows 54 emerge transversely in the inner passage 32 between the proximal shoulder 56 and the distal shoulder 66.

At its distal end, the distal portion 50 has retaining elements 68 for the tip 44, and an annular housing 70 for receiving a sealing gasket 72 (see FIG. 4).

The rotating tip 44 is intended to be mounted in rotation around the retaining elements 68 at the distal end, with interposition of the seal 72 received in the housing 70.

As illustrated by FIG. 5, the transverse tapping 44 protrudes laterally relative to the axis A-A' of the body 30, from the distal portion 50 of the tubular element 42. It has an axis B-B' inclined by a non-zero angle relative to the axis A-A'. The angle formed by the axis A-A' of the body 30 and the axis B-B' of the tapping is for example comprised between 45° and 90°.

The transverse tapping 44 delimits an auxiliary passage 74 for injecting liquid. The passage 74 emerges, upstream outside the device 14, and downstream in the inner passage 32.

The inner passage 32 extends between a proximal opening 76 situated at the proximal end of the tubular element 42, and a distal opening 78 situated at the tip 44.

The diameter of the passage 32 in the proximal portion 46, upstream from the locking shoulder 56, is greater than the diameter of the passage 32 in the intermediate portion 48, between the first locking shoulder 56 and the distal shoulder 66. The diameter of the passage 32 in the distal portion 50 is smaller than the diameter of the passage 32 in the intermediate portion 48.

Figure 6:
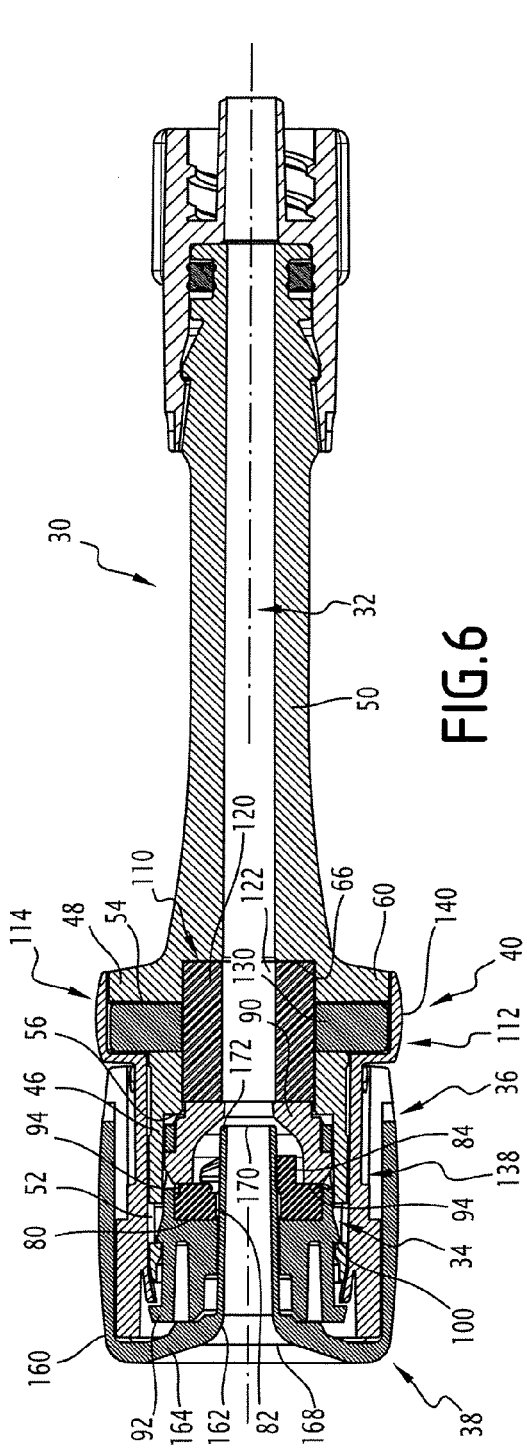
FIG. 6 is a view similar to FIG. 4, the opening member of the elastic valve having been actuated.

As illustrated by FIGS. 2, 3 and 6, the elastic valve 34 is made of a pierced body 80. The pierced body 80 is slitted in its center to delimit a central passage 82, which is sealed when idle.

Figure 11:
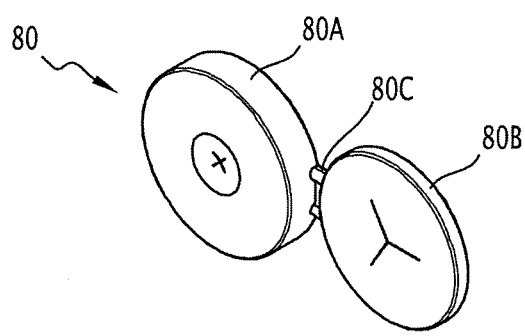
FIG. 11 is a perspective view of one embodiment of the valve before placement thereof in the device.

As illustrated in FIG. 11, the pierced body 80 is formed by an assembly of two discs 80A, 80B, advantageously connected to each other by a hinge 80C. The discs 80A, 80B are for example integral. The proximal disc 80A has a thickness that is greater than that of the distal disc 80B. The distal disc 80B is kept pressed against the proximal disc 80A by the axial locking mechanism 36.

The pierced body 80 thus includes a plurality of shutters 84, elastically movable between a sealed position of the central passage 82, in which they are deployed transversely relative to the axis of the pierced body 80, and a contracted position freeing the central passage 82.

The sealed position of the shutters 84 forms their idle configuration. The valve 34 is therefore capable of spontaneously returning to the sealed position when it is not biased.

In this example, the elastic valve 34 extends transversely at the proximal opening 76 of the passage 32. Alternatively, the valve 34 extends inside the passage 32.

In reference to FIGS. 2 and 4, the axial locking mechanism 36 includes a spacer 90 and a locking ring 92 placed on either side of the valve 34.

The valve 34 bears on a ring 94 of the spacer.

The locking ring 92 includes a proximal bearing ring 96 on the valve 34 and retaining members 98 to axially fix the locking ring 92 and the spacer 90, and to keep the valve 34 fixed between those elements.

The ring 92 includes outer radial stops 100 to fix it axially on the body 30.

The spacer 90 is wedged against the proximal openings 52 using two radial stops 100A.

The retaining members 98 are formed by tabs. The tabs 98 delimit housings 102 for receiving a stop 104 secured to the spacer 90.

Thus, the valve 34 is kept gripped between the spacer 90 and the locking ring 92. The locking ring 92 also provides axial locking by mechanical stacking of the valve 34 and the spacer 90 on the body 30.

In one alternative, the axial locking mechanism 36 has no spacer 90, the valve 34 being pressed directly on the shoulder 56.

According to the invention, the maintaining assembly 40 includes a compressible member 110 intended to engage with the material inserted into the passage 32 to retain it axially. The maintaining assembly 40 further includes at least one radial compression member 112, radially movable relative to the compressible member 110, and at least one actuating member 114 of each radial compression member 112.

The compressible member 110 is in this example formed by a cylindrical sleeve 120 delimiting a passage aperture 122 for the material. The sleeve 120 is advantageously made with a base of a flexible material, for example a material having a hardness comprised between 15 Shore A and 25 Shore A, in particular equal to 20 Shore A.

To accommodate different materials with varying radial expanses, the sleeve 120 has a radial thickness e1 greater than the transverse expanse of the aperture 122 that it delimits when idle. Thus, the thickness e1 of the sleeve 120 is for example greater than 1.5 times the half-diameter of the aperture 122.

In the embodiment shown in FIG. 2, the aperture 122 is also cylindrical. It has a diameter greater than 2.3 mm.

The thickness of the wall of the sleeve 122 is furthermore greater than 2 mm.

The length of the sleeve 120, considered between its ends along the axis A-A', is for example greater than 8 mm. It is in particular larger than 3 times the diameter of the aperture 122 when idle.

As will be seen below, the compressible member 110 can be deformed between a substantially cylindrical idle configuration, shown in FIGS. 1, 4, 5 and 6, in which the transverse section of the aperture 122 is maximal, and a radially deformed configuration, shown in FIG. 7, in which the transverse section of the aperture 122 is substantially zero, at least over an axial segment of the member 110.

In this example, the compressible member 110 is mounted in the passage 32 while being axially wedged between the distal shoulder 66 and the spacer 90. It extends across from the distal windows 54.

Figure 7:
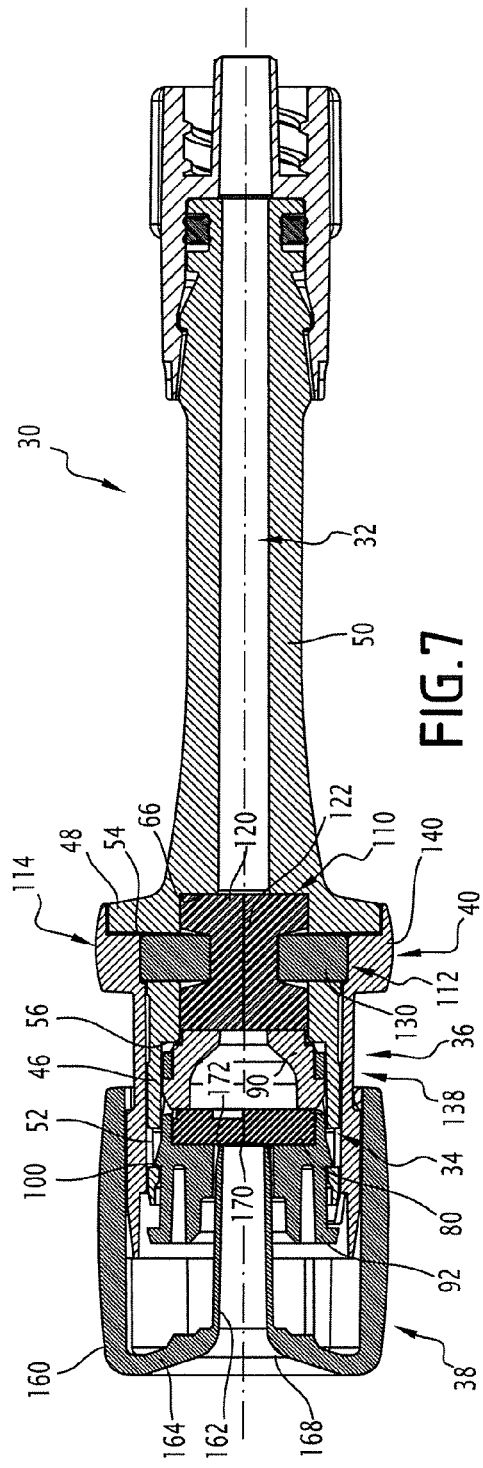
FIG. 7 is a view similar to FIG. 4, the actuating member of the compression member having been actuated.

In the example illustrated by FIGS. 2, 4 and 7, the axial maintaining assembly 40 includes a plurality of radial compression members 112. In particular, the assembly 40 includes at least two members 112 positioned on either side of the axis A-A', across from one another. The members 112 are situated in contact with an outer peripheral surface of the compressible member 110.

Each radial compression member 112 is formed by a jaw 130 radially movable relative to the body 30, between an idle retracted idle position, shown in FIG. 4, and a radially deployed position toward the axis A-A', shown in FIG. 7.

Each jaw 130 has an outer radial surface 132 intended to cooperate with the actuating member 114, and an inner radial surface 134 intended to press on the compressible member 110.

In the example shown in FIG. 2, the inner radial surface 134 of each jaw 130 is concave. The concave inner surface 134 thus has a shape substantially complementary to the convex outer peripheral surface of the sleeve 120 on which it is pressed.

The outer radial surface 132 is advantageously convex.

Each jaw 130 is inserted through a distal window 54. It is guided in radial translation toward the axis A-A' in the window 54, between the idle retracted position and the radially deployed position.

In the idle retracted position, as shown in FIG. 4, each jaw 130 is advantageously positioned separated from the passage 32. It is pressed on the outer peripheral surface of the compressible member 110, without exerting significant force on this surface. The compressible member 110 is therefore kept in its idle configuration.

In the deployed position, each jaw 130 is radially deployed toward the axis A-A' in the inner passage 32. It radially compresses, toward the axis A-A', the compressible member 110 to produce local gripping of the sleeve 120 and sealing of the aperture 122.

In this example, the actuating member 114 is mounted movably relative to the body 30, exclusively in rotation around the axis A-A', between a first idle position and a second actuating position of each radial compression member 112.

The actuating member 114 is generally formed by a tubular element 138. It includes a distal actuating wheel 140 and, in this example, a proximal portion 142 for guiding and blocking the valve opening member 38.

The actuating member 114 inwardly has an actuating cam 144 for each radial compression member 112.

The tubular member 138 is mounted in rotation on the body 30 around the axis A-A' while being guided by the collar 60.

The wheel 140 protrudes radially relative to the proximal portion 142. It outwardly covers the collar 60. It is provided with outer orifices for receiving the fingers of an user.

Figure 10:
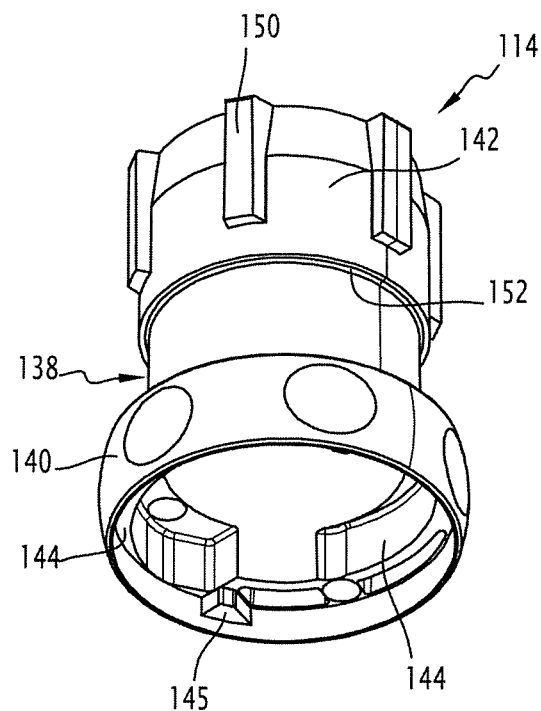
FIG. 10 is a perspective bottom view of the actuating member of the compression member.

The wheel 140 has complementary stops 145, visible in FIG. 10, intended to cooperate with the end-of-travel stops 64 to limit the travel of the actuating member 114 between the first position and the second position.

Each cam 144 has a radial expanse increasing toward the axis A-A' while moving angularly around the axis A-A'. It is positioned in contact with a radial compression member 112.

Thus, each cam 144 is capable of cooperating with the compression member 112 and gradually moving that member 112 radially toward the axis A-A' during the rotation of the actuating member 114 around the axis A-A'.

In this example, the proximal portion 142 comprises guides 150 for the movement of the opening member 38 and an axial stop 152 for retaining the member 38. The guides 150 extend parallel to the axis A-A'. They are formed by longitudinal ribs. The annular stop 152 is formed by an outer shoulder.

The opening member 38 of the valve 34 here is mounted sliding on the actuating member 114. It has an outer peripheral wall 160, an inner actuating sleeve 162, and a skirt 164 connecting the peripheral wall 160 to the actuating sleeve 162.

The peripheral wall 160 is slidingly mounted along the axis A-A' relative to the body 30.

In this example, the wall 160 caps the proximal portion 142 of the actuating member 114. It has a distal locking rim 166 intended to cooperate axially with the retaining stop 152.

The actuating sleeve 162 coaxially extends with the axis A-A' in the peripheral wall 160. It emerges through a proximal opening 168 for inserting the material 12 through a distal opening 170 situated at its free edge 172.

The opening member 38 is movable in translation along the axis A-A', between an idle proximal position and a distal position opening the valve 34.

In the proximal position, shown in FIG. 5, the rim 166 is positioned in contact with the retaining stop 152 to limit the proximal movement of the opening member 38. The distal edge 172 of the actuating sleeve 162 is situated in contact with the valve 34, without being inserted inside the central passage 82.

The shutters 36 of the valve 34 then occupy their idle deployed position. The valve 34 seals the passage 32.

In the distal position, shown in FIG. 6, the opening member 38 has moved along the axis A-A' relative to the body 30 toward the distal end of the body 30.

The rim 166 has separated from the stop 152 while moving toward the distal end of the body 30.

In this example, the rim 166 axially abuts against the wheel 140. The skirt 164 abuts against the ring 92.

The sleeve 162 has been inserted through the central passage 82 of the valve 34 while separating the shutters 84 from the axis A-A'.

A freed continuous passage therefore extends from the proximal opening 168, through the sleeve 162, as far as the distal opening 170 to emerge in the passage 32.

In this position, the valve 34 is open and the medical material 12 can be inserted through the device 14.

The operation of the kit 10 according to the invention will now be described.

Initially, a guide catheter (not shown) is inserted into the vascular system of the patient.

The hemostasis valve device 14 is then connected to a free end of the guide catheter using the rotating tip 44.

Likewise, a liquid injection assembly, for example a coronarography set, is mounted on the tapping 44.

Next, debubblizing of the device 14 is done, to avoid introducing air into the vascular system.

Then, the medical material 12 is inserted through the inner passage 32. To that end, the operator first actuates the opening member 38 to cause it to go from its proximal position to its distal position.

During this transition, he inserts the sleeve 162 through the central passage of the valve 34 and frees a continuous passage for the insertion of the material 12. Then, he causes the material 12 to pass through the sleeve 162 and through the inner passage 32 of the body 30, to reach the distal opening 78.

When the material 12 has been inserted, the operator returns the opening member 38 to its proximal position, which causes the shutters 84 of the valve 34 to go toward their deployed position through elastic biasing. The shutters 84 press sealably around the material 12, ensuring sealing toward the distal end of the body 30.

Once that is done, the operator can then modify the axial position of the medical material 12 while pulling or pushing axially the material 12 through the valve 34, without any risk of leaking.

Once the material 12 is correctly positioned, the operator maneuvers the actuating member 114. In this example, he rotates it around the axis A-A', with no translational movement. This movement is therefore extremely easy and quick to perform relative to screwing.

During this movement, the cam 144 pivots around the axis A-A' and moves angularly relative to each radial compression member 112. The radial compression member 112 is therefore pushed radially toward the axis A-A' by the cam 144. This causes it to be pressed on the outer surface of the compressible member 110 and causes local compression of the compressible member 110 toward the radially deformed configuration.

The section of the central aperture 122 delimited by the sleeve 120 therefore decreases across from each member 112, until the sleeve 120 is pressed around the medical material 12 to maintain it axially.

The sleeve 120 being made with a base of a sufficiently deformable and thick enough material, the operator therefore continues the rotating movement of the actuating member 114 until reaching the end of travel, in which the end-of-travel stops 64 come into contact with the complementary stops present in the actuating member 114.

In light of the significant thickness of the sleeve 120 and the corresponding size of the aperture 122, the compressible member 110 is capable of adapting to medical material with varying radial expanses, and providing sufficient gripping irrespective of the radial expanse of the material.

Furthermore, whatever the radial expanse of the material 12 inserted through the aperture 122, the operator moves the actuating member 114 until its end of travel, which in all cases guarantees good strength of the material.

Then, a medical intervention may be performed using the material 12.

Figure 8:
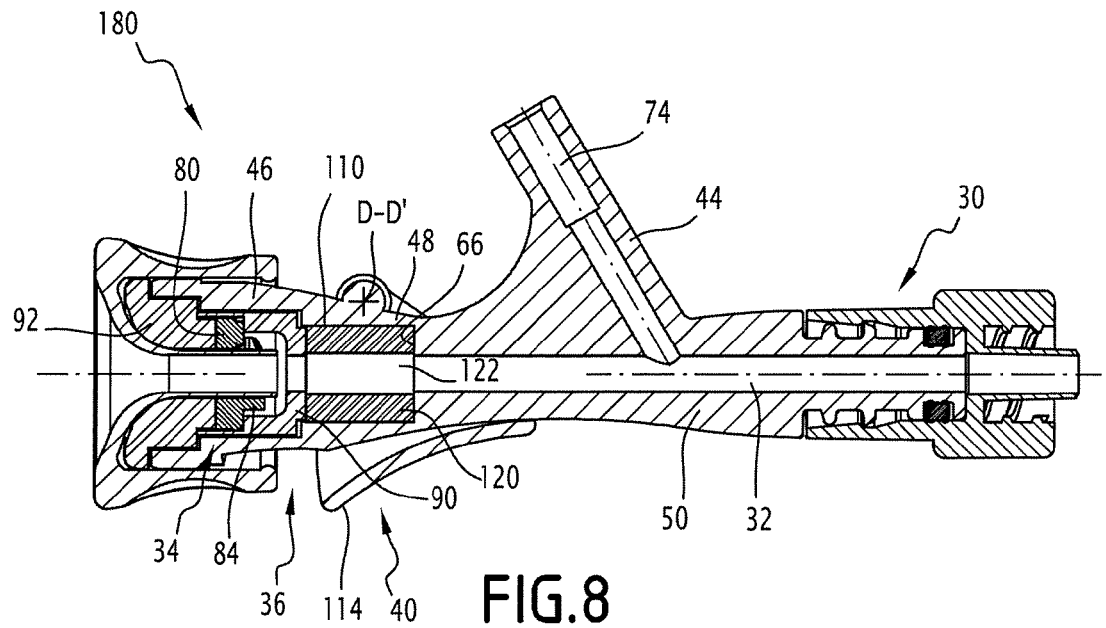
FIG. 8 is a view similar to FIG. 6 of a second hemostasis valve device according to the invention.
Figure 9:
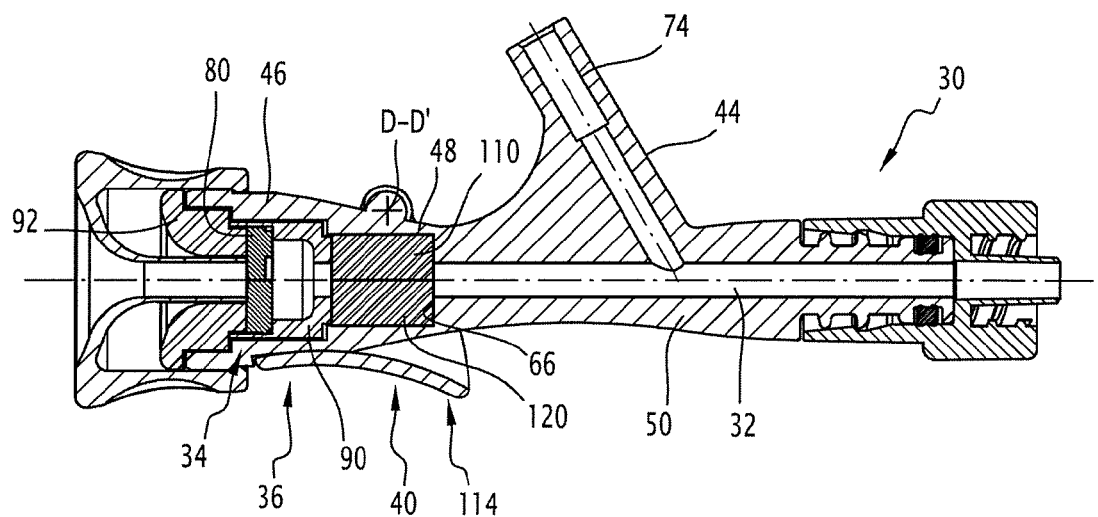
FIG. 9 is a view similar to FIG. 7 of the second valve device according to the invention.

A second kit 180 according to the invention is illustrated by FIGS. 8 and 9.

Unlike the first kit 10, the actuating member 114 is formed by a button 182 pivoting around an axis D-D' perpendicular to the axis A-A' of the body 30. As before, no screwing movement is necessary to cause the actuating member 114 to go from its first position to its second position. A simple rotation around the axis D-D' suffices to perform that transition.

In this kit 180, the opening member 38 can be moved independently of the actuating member 114. It is thus mounted movable in translation directly on the body 30.

As in the device 14, there are two compression members 112 to close and open the aperture 122. The movement of these members 112 is commanded by switching the actuating member 114, which forms a rocker button.

More generally, this independent arrangement of the opening member 38 may also apply to the device described in FIGS. 1 to 7.

In one alternative, in light of the thickness of the sleeve 120, and its deformability, the device 14 is capable of axially locking a plurality of materials 12 mounted in parallel relative to one another in the inner passage 32, for example a guide wire, a guide wire and a catheter positioned parallel to the guide wire, two guide wires and a catheter, two guide wires and two catheters, or even a guide wire and a cutter of the Rotablator® type.

In one alternative, the device 14 includes the presence of means for locking the actuating member 114 in its second position, at the end of travel. This facilitates maneuvering by the operator, and guarantees that the operator performs effective tightening of the medical material 12.

Advantageously, the actuating member 114 of the compressible member 110 is biased toward the first idle position in any intermediate position comprised between the first idle position and the second actuating position. This bias results from the local compression of the compressible member 110 by the jaws 130 in the second position.

Thus, the means for locking in position keep the actuating member 114 in the second position against the bias from the actuating member 114 toward the first position.

The first position and the second position of the actuating member constitute the only two stable positions of the actuating member 114, which operates like a switch.

Thus, during operation, if the user unlocks the actuating member 114 by releasing the locking means, the actuating member 114 will spontaneously be brought toward the first position by deploying the compressible member 110 acting on the jaws 130 to deploy them radially, then by cooperation between the jaws 130 and the actuating member 114.

When the actuating member is movable in rotation around the axis A-A', its angular travel around the axis A-A' between the first position and the second position is generally comprised between 90° and 150°. This travel is preferably comprised between 110° and 120° to allow simple and fast actuation of the member 114.

This optimizes the movement of the jaws 130 in the windows 54 between their retracted idle position and their radially deployed position toward the longitudinal axis A-A'.

Preferably, and as illustrated in FIG. 2, each jaw 130 is movable in radial translation along an axis perpendicular to the axis A-A' intersecting the axis A-A'.

The jaws 130 are separate, and have a maximal angular expanse smaller than 90°. They therefore make it possible to apply a very concentrated radial compression force on the radially compressible member 110, with a minimal rotation of the actuating member 114.

In another alternative, the radially compressible member 110 is formed from a material having a hardness comprised between 25 Shore A and 40 Shore A, advantageously between 26 Shore A and 35 Shore A.

The invention claimed is:

1. A hemostasis valve device intended for inserting a medical material into a patient, comprising:
   a hollow body delimiting an inner passage for inserting the medical material extending between a proximal opening and a distal opening;
   a sealing valve positioned in the inner passage, the sealing valve having a central passage that is sealed when idle;
   an opening member opening the central passage of the sealing valve, movable relative to the body between an idle position, in which the sealing valve is sealed, and an open position of the sealing valve;
   wherein the hemostasis valve device further includes a maintaining assembly maintaining the medical material in position in the inner passage of the body, the maintaining assembly including:
   a radially compressible member positioned in the inner passage, the compressible member delimiting, when idle, a through passage aperture for receiving the medical material therethrough;
   at least two opposite compression members for radially compressing the compressible member, radially movable relative to an axis of the through passage aperture to outwardly compress the compressible member; and
   an actuating member movable relative to the body to cause the at least two opposite compression members to go from a radially retracted position, in which the section of the through passage aperture is maximal, to a position that is radially deployed in the compressible member, in which the section of the through passage aperture is minimal;
   the actuating member being mounted movable relative to the body between a first idle position, in which each compression member is in its retracted position, and a second actuating position, in which each compression member is in its radially deployed position;
   the actuating member being capable of simultaneously moving the at least two opposite compression members from radially retracted positions toward radially deployed positions;
   each compression member being formed by a jaw that is radially movable relative to the body between an idle retracted position and a position that is deployed radially toward a longitudinal axis of the body, each jaw being inserted through a distal window of the body and being guided in radial translation toward a longitudinal axis in the window between the idle retracted position and the radially deployed position; and
   a locking assembly for locking the actuating member in its second actuating position;
   wherein in any intermediate position comprised between the first idle position and the second actuating position, the actuating member is biased toward the first idle position, the locking assembly maintaining the actuating member in the second actuating position against the bias of the actuating member toward the first idle position, the first idle position and the second actuating position constituting the only two stable positions of the actuating member.

2. The device according to claim 1, wherein the actuating member is movable in rotation around the longitudinal axis of the body, an angular travel of the actuating member around the longitudinal axis of the body advantageously being comprised between 90° and 150°.

3. The device according to claim 2, wherein the actuating member is movable only in rotation around the longitudinal axis of the body, without translation relative to the body.

4. The device according to claim 1, wherein the compressible member includes an elastic sleeve which, when idle, delimits the through passage aperture, a thickness of the sleeve, considered perpendicular to the axis of the through passage aperture, being greater than 50% of a maximal transverse expanse of the through passage aperture.

5. The device according to claim 1, wherein the compressible member is formed from a material having a hardness comprised between 15 Shore A and 40 Shore A.

6. The device according to claim 1, wherein each jaw has a concave surface intended to bear on a convex outer surface of the compressible member.

7. The device according to claim 1, wherein the opening member of the sealing valve is mounted movable in translation on the actuating member, the opening member being movable jointly with the actuating member during its movement between the first idle position and the second actuating position.

8. The device according to claim 1, wherein the sealing valve includes a pierced body, the pierced body being formed by two discs assembled one on the other, the pierced body delimiting a plurality of sealing shutters, the opening member comprising a hollow actuating sleeve inserted between the plurality of sealing shutters to open the central passage of the sealing valve.

9. The device according to claim 1, wherein the sealing valve is positioned between the proximal opening of the body and the compressible member.

10. The device according to claim 1, wherein the actuating member is mounted in rotation relative to the body around an axis perpendicular to the longitudinal axis of the body.

11. The device according to claim 1, wherein the at least two opposite compression members consist of two opposite compression members positioned on either side of the longitudinal axis of the body, across from one another, each jaw being inserted through a distal window, the body delimiting two distal windows positioned across from each other, on either side of a longitudinal axis of the body.

12. The device according to claim 1, wherein the actuating member is movable in radial translation along an axis perpendicular to the longitudinal axis of the body between the retracted position and the deployed position.

13. The device according to claim 1, wherein the compressible member is formed from a material having a hardness between 15 Shore A and 25 Shore A.

14. The device according to claim 1, wherein the compressible member is formed from a material having a hardness between 26 Shore A and 35 Shore A.

15. The device according to claim 1, wherein the opening member is engaged with the device and the actuating member further comprises a proximal portion comprising an axial stop for retaining the opening member, the opening member comprising an outer peripheral wall having a distal locking rim intended to cooperate axially with the retaining stop.

16. A hemostasis valve device intended for inserting a medical material into a patient, comprising:
a hollow body delimiting an inner passage for inserting the medical material extending between a proximal opening and a distal opening;
a sealing valve positioned in the inner passage, the sealing valve having a central passage that is sealed when idle;
an opening member opening the central passage of the sealing valve, movable relative to the body between an idle position, in which the sealing valve is sealed, and an open position of the sealing valve;
wherein the hemostasis valve device further includes a maintaining assembly maintaining the medical material in position in the inner passage of the body, the maintaining assembly including:
a radially compressible member positioned in the inner passage, the compressible member delimiting, when idle, a through passage aperture for receiving the medical material therethrough;
at least two opposite compression members for radially compressing the compressible member, radially movable relative to an axis of the through passage aperture to outwardly compress the compressible member; and
an actuating member movable relative to the body to cause the at least two opposite compression members to go from a radially retracted position, in which the section of the through passage aperture is maximal, to a position that is radially deployed in the compressible member, in which the section of the through passage aperture is minimal;
the actuating member being capable of simultaneously moving the at least two opposite compression members from radially retracted positions toward radially deployed positions;
each compression member being formed by a jaw that is radially movable relative to the body between an idle retracted position and a position that is deployed radially toward a longitudinal axis of the body, each jaw being inserted through a distal window of the body and being guided in radial translation toward a longitudinal axis in the window between the idle retracted position and the radially deployed position;
each distal window being formed in and bounded on all sides by the body forming a closed contour.

17. A hemostasis valve device intended for inserting a medical material into a patient, comprising:
a hollow body delimiting an inner passage for inserting the medical material extending between a proximal opening and a distal opening;
a sealing valve positioned in the inner passage, the sealing valve having a central passage that is sealed when idle;
an opening member opening the central passage of the sealing valve, movable relative to the body between an idle position, in which the sealing valve is sealed, and an open position of the sealing valve;
wherein the hemostasis valve device further includes a maintaining assembly maintaining the medical material in position in the inner passage of the body, the maintaining assembly including:
a radially compressible member positioned in the inner passage, the compressible member delimiting, when idle, a through passage aperture for receiving the medical material therethrough;
at least two opposite compression members for radially compressing the compressible member, radially movable relative to an axis of the through passage aperture to outwardly compress the compressible member; and an actuating member comprising a proximal portion comprising guides and the opening member comprising grooves complementary to the guides, the guides and the grooves being placed opposite to each other, the opening member being able to rotate the actuating member by virtue of the guides and the grooves;

the actuating member being movable relative to the body to cause the at least two opposite compression members to go from a radially retracted position, in which the section of the through passage aperture is maximal, to a position that is radially deployed in the compressible member, in which the section of the through passage aperture is minimal;

the actuating member being capable of simultaneously moving the at least two opposite compression members from radially retracted positions toward radially deployed positions;

each compression member being formed by a jaw that is radially movable relative to the body between an idle retracted position and a position that is deployed radially toward a longitudinal axis of the body, each jaw being inserted through a distal window of the body and being guided in radial translation toward a longitudinal axis in the window between the idle retracted position and the radially deployed position;

the actuating member being movable in rotation around a longitudinal axis of the body between a first idle position and a second actuating position of each radial compression member, the actuating member being made in a single piece.

* * * * *